United States Patent [19]

Yoshinaga et al.

[11] Patent Number: 4,876,027

[45] Date of Patent: Oct. 24, 1989

[54] OPTICALLY ACTIVE COMPOSITION, MESOMORPHIC COMPOUND AND LIQUID CRYSTAL DEVICE

[75] Inventors: Kazuo Yoshinaga, Machida; Kazuharu Katagiri, Tama; Toyoko Kobayashi, Kawasaki; Kenji Shinjo, Yokohama, all of Japan

[73] Assignee: Canon Kabushiki Kaisha, Tokyo, Japan

[21] Appl. No.: 302,145

[22] Filed: Jan. 27, 1989

Related U.S. Application Data

[63] Continuation of Ser. No. 900,712, Aug. 27, 1986, abandoned.

[30] Foreign Application Priority Data

Sep. 4, 1985 [JP] Japan ............................ 60-193831
Dec. 19, 1985 [JP] Japan ............................ 60-284240

[51] Int. Cl.[4] ..................... G02F 1/13; C09K 19/20; C09K 19/12; C09K 19/06; C07C 153/07
[52] U.S. Cl. ........................... 252/299.65; 252/299.01; 252/299.64; 252/299.67; 252/299.6; 350/350 R; 350/350 S; 558/257
[58] Field of Search ............... 252/299.67, 299.65, 252/299.64, 299.5, 299.6, 299.01; 350/350 R, 350 S; 558/257

[56] References Cited

U.S. PATENT DOCUMENTS

| 4,137,250 | 1/1979 | Reynolds | 252/299.67 |
|---|---|---|---|
| 4,162,988 | 7/1979 | Maze et al. | 252/299.65 |
| 4,427,569 | 1/1984 | Margerum et al. | 252/299.65 |
| 4,596,667 | 6/1986 | Inukai et al. | 252/299.65 |
| 4,613,209 | 9/1986 | Goodby et al. | 252/299.65 |
| 4,615,586 | 10/1986 | Geary et al. | 252/299.65 |
| 4,653,866 | 3/1987 | Era et al. | 252/299.65 |

FOREIGN PATENT DOCUMENTS

| 2603293 | 8/1977 | Fed. Rep. of Germany | 252/299.67 |
|---|---|---|---|
| 56-108761 | 8/1981 | Japan | 252/299.67 |
| 59128357 | 7/1984 | Japan | 252/299.67 |

OTHER PUBLICATIONS

Kim, Y. B., et al., Mol. Cryst. Liq. Cryst. 36, pp. 293–306 (1976).
Reynolds, R. M. et al., Mol. Cryst. Liq. Cryst. 36, pp. 41–50 (1976).
Heppke, G., et al., Z. Naturforsch, vol. 32a, pp. 899–901 (1977).
Tinh, N. H., et al., Mol. Cryst. Liq. Crys., Lett. Sect., vol. 4(34), pp. 93–98 (1987).

*Primary Examiner*—Teddy S. Gron
*Attorney, Agent, or Firm*—Fitzpatrick, Cella, Harper & Scinto

[57] ABSTRACT

4-Alkoxybenzenethiol, bis-(4-alkoxyphenyl)disulfide, and mesomorphic compound deviced therefrom represented by the formula:

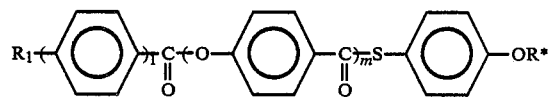

wherein $R_1$ is an alkyl or alkoxy group having 1–18 carbon atoms, $R^*$ is an alkyl group having 4–12 carbon atoms including an asymmetric carbon atom, $l=1$ or 2, and $m=0$ or 1.

38 Claims, 1 Drawing Sheet

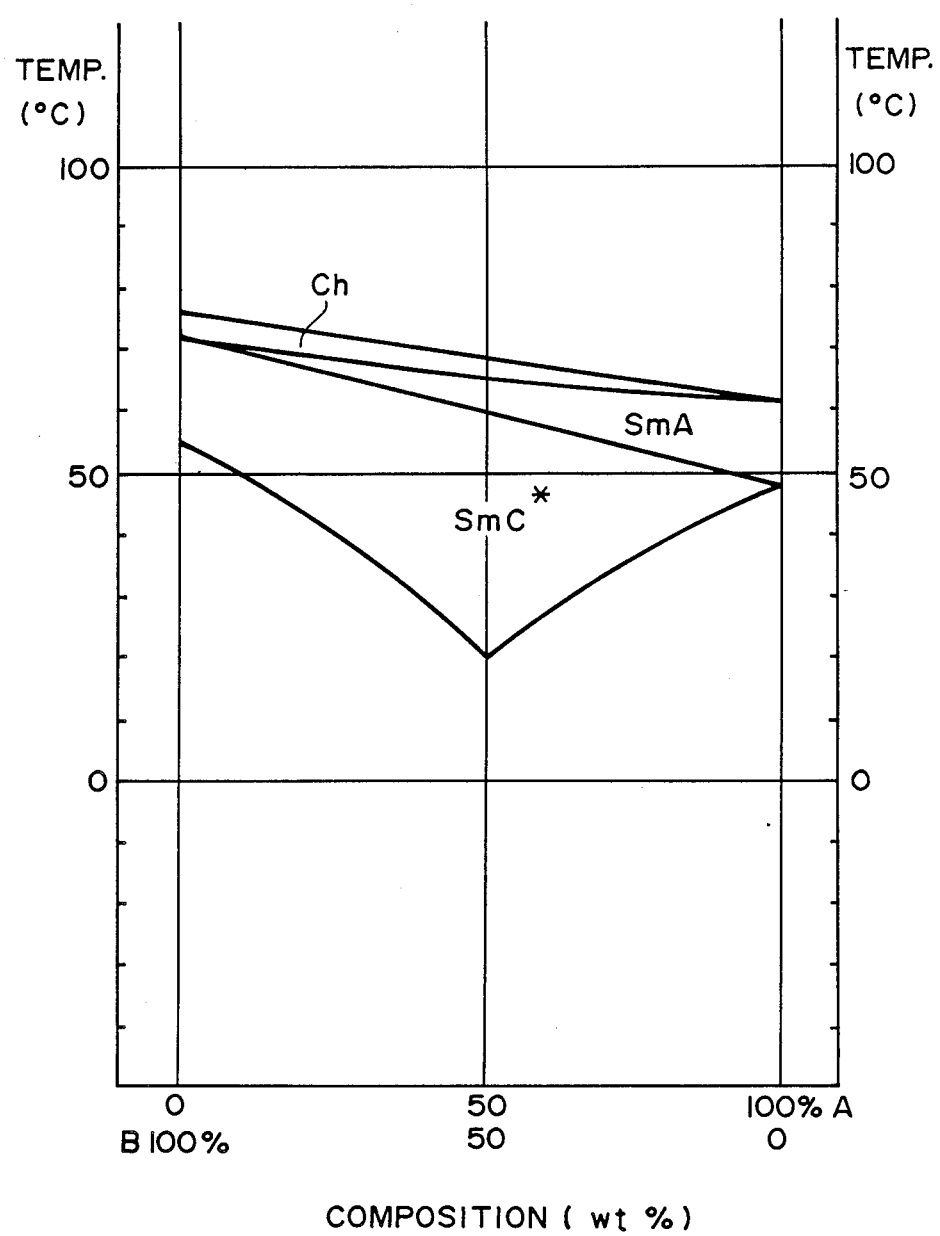

OPTICALLY ACTIVE COMPOSITION, MESOMORPHIC COMPOUND AND LIQUID CRYSTAL DEVICE

This application is a continuation of application Ser. No. 900,712, filed Aug. 27, 1986, now abandoned.

FIELD OF THE INVENTION ARE RELATED ART

The present invention relates to a novel optically active compound and mesomorphic compound and, more particularly, to an optically active mesomorphic compound, a chiral smectic liquid crystal composition containing the same and a liquid crystal device using the liquid crystal composition.

There are well known types of liquid crystal devices using TN (twisted nematic) type liquid crystals as shown, for example, in "Voltage-Dependent Optical Activity of a Twisted Nematic Liquid Crystal" by M. Schadt and W. Helfrich, Applied Physics Letters, Vol. 18, No. 4 (Feb. 15, 1971), pp. 127-128. In such of liquid crystal devices, the number of picture elements have been restricted, because there is a problem that a crosstalk phenomenon occurs when a device of a matrix electrode structure with a high density of picture elements is driven according to a time-sharing of time-division driving scheme. Further, their uses as displays have been limited because of slow electric field response and poor visual angle characteristics.

As another type of liquid crystal device is one comprising a plurality of picture elements each connected to and subject to switching by a thin film transistor as a switching element. This type of liquid crystal device, however, is accompanied with problems such that production of thin film transistors on a substrate is very complicated, and production of a display device with a large picture area or screen is difficult.

In order to obviate the above-mentioned drawbacks of conventional types of liquid crystal devices, Clark and Lagerwall proposed the use of a liquid crystal device wherein a ferroelectric liquid crystal is disposed in a thin layer having a thickness less than 5 times that of the spiral pitch thereof so that its spiral structure is unwound to develop a bistability (e.g., U.S. Pat. No. 4,367,924).

As the bistable liquid crystal, a ferroelectric crystal showing a chiral smectic C phase (SmC*) or H phase (SmH*) is generally used.

Such a ferroelectric liquid crystal has a rapid response speed on account of its spontaneous polarization, can exhibit a memorizable bistable state and further has a excellent vision angle characteristic, and therefore is suitable for a display of large capacity and picture area.

On the other hand, as optically active intermediates for synthesizing functional materials necessary for such optical devices characterized by optical activity, compounds are known such as 2-methylbutanol, sec-octyl alcohol, sec-butyl alcohol, p-(2-methylbutyl)benzoic acid chloride, sec-phenethyl alcohol, amino acid derivatives, camphor derivatives and cholesterol derivatives.

These intermediates involve respective problems as follows. Thus, optically active chain hydrocarbon derivatives are difficult to modify their structures and very expensive except for a particular class thereof. Although amino acid derivatives are relatively cheap and easy to modify their structures, the N-hydrogens therein are chemically active and liable to cause hydrogen bonding or other chemical reactions so that the performances of the resultant functional material can be restricted thereby. Camphor derivatives and cholesterol derivatives are difficult to modify and steric hindrance is liable to provide ill effects to the performance of the resultant functional materials.

These problems have provided great difficulties in developing various functional materials.

SUMMARY OF THE INVENTION

A principal object of the present invention is to provide a solution of the above described problems. More specifically, an object of the invention is to provide a compound which can be combined with an intermediate for a functional material having appropriate intermolecular force and shape without imparting its optical activity, and which is therefore susceptible of arbitrary molecular designing.

A further object of the present invention is to provide a mesomorphic compound having a smectic liquid crystal phase around room temperature or having an effect of lowering and enlarging the temperature range of a chiral smectic C-phase (SmC*) when mixed as a component, a liquid crystal composition containing at least one species of such a mesomorphic compound, and a liquid crystal device using the liquid crystal composition.

Another specific object of the present invention is to provide a mesomorphic compound capable of readily changing the length of the alkyl chain and therefore capable of controlling a kind of liquid crystal phase to be developed in the liquid crystal state and a temperature range therefor as shown by H. Arnold: Z. Phys. Chem., 226, 146 (1964), and a liquid crystal composition containing at least one of such mesomorphic compounds. A further object of the present invention is to provide a compound capable of easily controlling the hydrophobic group and being stably formed into a film when applied to the LB (Langmuir-Blodget) film process for preparing an accumulation of single molecular films.

More specifically, the present invention provides an optically active 4-alkoxybenzenethiol represented by the following formula (II):

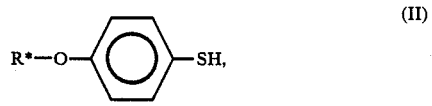

(II)

wherein R* is an alkyl group having an asymmetric carbon atom, and a liquid crystal composition containing at least one species of the thiol.

Further, the present invention provides an optically active bis(4-alkoxyphenyl)disulfide represented by the following formula (III):

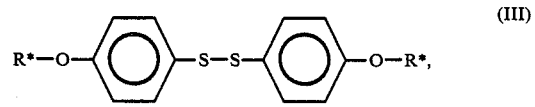

(III)

wherein R* is an alkyl group having an asymmetric carbon atom, and a liquid crystal composition containing at least one species of the disulfide.

Furthermore, the present invention provides an optically active mesomorphic compound represented by the following formula (I):

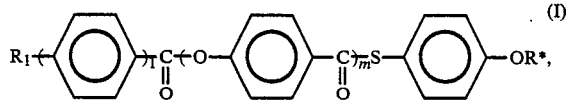

wherein $R_1$ is an alkyl or alkoxy group having 1–18 carbon atoms, $R^*$ is an alkyl group having 4–12 carbon atoms including an asymmetric carbon atom, $l = 1$ or 2, and $m = 0$ or 1.

The present invention further provides a liquid crystal composition containing at least one species of the optically active mesomorphic compound, and a liquid crystal device using the liquid crystal composition.

The above mentioned and other objects and features of the invention will be better understood upon consideration of the following detailed description concluding with specific examples of practice. In the following description, "%" and "parts" used to indicate an amount or composition are by weight unless otherwise noted specifically.

BRIEF DESCRIPTION OF THE DRAWING

The sole FIGURE in the drawing is a phase diagram showing the phase transition temperatures of a mesomorphic compound of the present invention prepared in Examples 6 and a liquid crystal composition containing the mesomorphic compounds prepared in Example 16 versus the proportions of the mesomorphic compounds.

DETAILED DESCRIPTION OF THE INVENTION

As the compounds represented by the above formulae (II) and (III) have an asymmetric carbon atom and a thiol group by the medium of a benzene ring, they can readily provide various derivatives with a thiol-carboxylic acid-ester bond, a sulfide bond, a sulfoxide bond, etc., without losing their optical activity, and so they are expected to be very extensively utilized. Up to now, however, no optically active compounds as represented by the formulae (II) or (III) have been known.

Based on the above knowledge, we have made an extensive study and, as a result thereof, have succeeded in synthesis of compounds represented by the formulae (II) and (III) to accomplish the present invention.

A novel optically active compound represented by the above formulae (II) or (III) may be added to a nematic liquid crystal to effectively prevent generation of reverse domain in a twisted nematic (TN) type cell. Further, it can be added to a nematic liquid crystal to provide a chiral smectic liquid crystal which may be used in a phase transition-type liquid crystal or a White-Taylor-type guest-host liquid crystal device.

The optically active compound may also be added to a liquid crystal composition to be used in a device wherein the ferroelectricity in a chiral smectic phase is utilized in order to improve the characteristics. On the other hand, the optically active compound represented by formulae (II) or (III) according to the present invention may also be added to a smectic liquid crystal as shown below to form a ferroelectric chiral smectic phase.

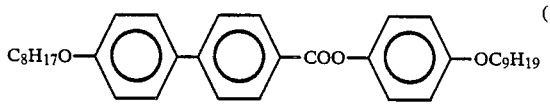

-continued (4-nonyloxyphenyl)-4'-octyloxybiphenyl-4-carboxylate

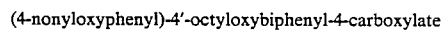

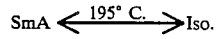

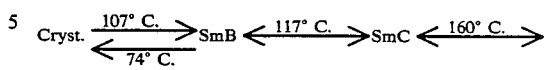

4,4'-decyloxyazoxybenzene

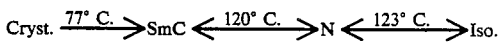

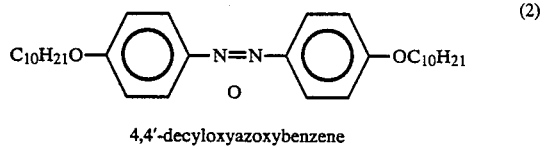

2-(4'-hexyloxyphenyl)-5-(4'-hexyloxyphenyl)-pyrimidine

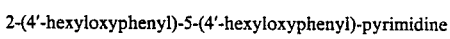

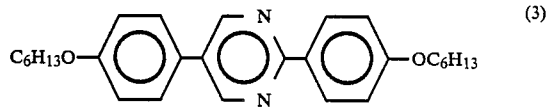

2-(4'-octyloxyphenyl)-5-nonylpyrimidine

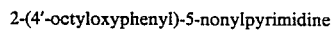

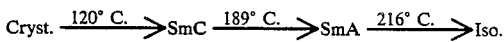

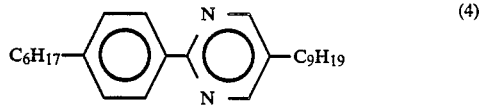

4'-pentyloxyphenyl-4-octyloxybenzoate

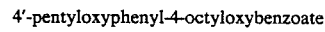

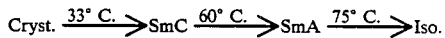

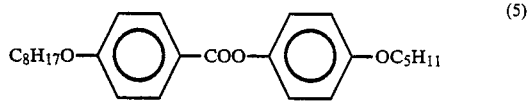

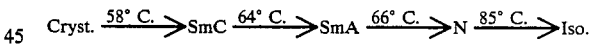

As described above, the optically active compound represented by formulae (II) or (III) is very effective in improving the performances of a ferroelectric liquid crystal device and a TN-type liquid crystal device.

Next, a process for synthesizing the optically active compounds according to the present invention will be described.

In order to produce the optically active (4-alkoxy)-benzenethiols represented by formula (I), an optically active aliphatic alcohol may be used first of all. Specific examples thereof include: 3-methylpentanol, 4-methylhexanol, 1-methylheptanol, 2-methylbutanol, 2-methyloctanol, 2-methylnonanol, 2-methyldecanol, etc.

The optically active alcohol is halogenized or sulfonated and connected with phenol through an ether bond to form an optically active alkoxybenzene, which is then chlorosulfonylated. The thus obtained (4-alkoxy)phenylsulfonylchloride is reduced to form an optically active (4-alkoxy)benzenethiol of formula (II).

The optically active bis(4-alkoxyphenyl)disulfides of formula (III) may be obtained by changing, e.g., the conditions for reducing the optically active (4-alkoxy)- phenylsulfonylchlorides obtained in the same manner as above.

The above mentioned synthesis processes may be summarized as follows:

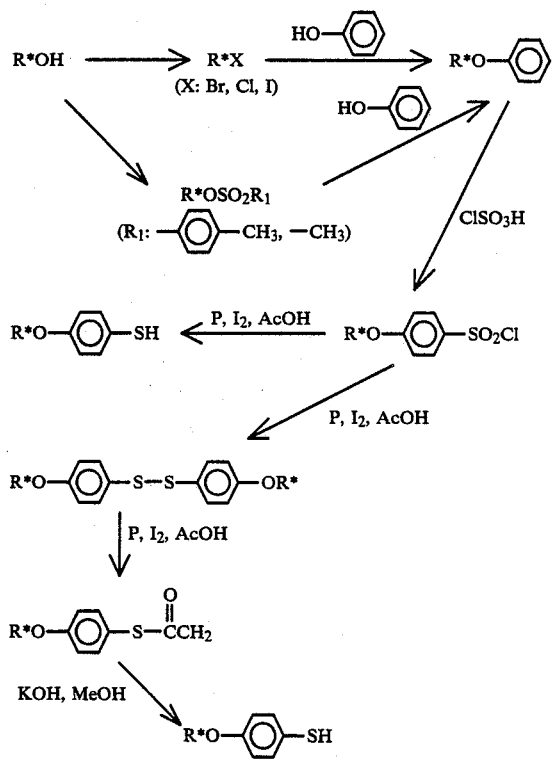

Specific examples of the thus obtained optically active compounds include the following:
(+)-4-(2'-methyl-butoxy)benzenethiol,
(+)-4-(1'-methyl-propoxy)benzenethiol,
(−)-4-(1'-methyl-propoxy)benzenethiol,
(+)-4-(1'-methylhexyloxy)benzenethiol,
(−)-4-(1'-methylhexyloxy)benzenethiol,
(+)-4-(1'-methylpentyloxy)benzenethiol,
(−)-4-(1'-methylpentyloxy)benzenethiol,
(+)-4-(1',3'-dimethylpropoxy)benzenethiol,
(−)-4-(1',3'-dimethylpropoxy)benzenethiol,
(+)-4-(1'-methylheptyloxy)benzenethiol,
(−)-4-(1'-methylheptyloxy)benzenethiol,
(+)-4-(1'-methylbutoxy)benzenethiol,
(−)-4-(1'-methylbutoxy)benzenethiol,
(+)-4-(3'-methylpentyloxy)benzenethiol,
(−)-4-(2'-methyloctyloxy)benzenethiol,
(−)-4-(2'-methylnonyloxy)benzenethiol,
(−)-4-(2'-methyldecyloxy)benzenethiol,
(+)-4-(4'-methylhexyloxy)benzenethiol,
(+)-bis(4-(2'-methylbutoxy)phenyl)disulfide,
(+)-bis(4-(1'-methylpropoxy)phenyl)disulfide,
(−)-bis(4-(1'-methylpropoxy)phenyl)disulfide,
(+)-bis(4-(1'-pentyloxy)phenyl)disulfide,
(−)-bis(4-(1'-pentyloxy)phenyl)disulfide,
(+)-bis(4-(1',3'-dimethylpropoxy)phenyl)disulfide,
(−)-bis(4-(1',3'-dimethylpropoxy)phenyl)disulfide,
(+)-bis(4-(1'-methylheptyloxy)phenyl)disulfide,
(−)-bis(4-(1'-methylheptyloxy)phenyl)disulfide,
(+)-bis(4-(1'-methylbutoxy)phenyl)disulfide,
(−)-bis(4'(1'-methylbutoxy)phenyl)disulfide,
(+)-bis(4-(3'-methylpentyloxy)phenyl)disulfide,
(−)-bis(4-(2'-methyloctyloxy)phenyl)disulfide,
(−)-bis(4-(2'-methylnonyloxy)phenyl)disulfide,
(−)-bis(4-(2'-methyldecyloxy)phenyl)disulfide,
(+)-bis(4-(4'-methylhexyloxy)phenyl)disulfide.

The thus obtained optically active compound represented by formulae (II) or (III) is effective in preventing occurrence of reverse domain when added to a nematic liquid crystal. In this case, it is preferred to use the compound in a proportion of 0.01–50 wt.% of the liquid crystal composition.

Further, the optically active compound may be added to a nematic liquid crystal to provide a chiral smectic liquid crystal composition which may be used in a phase transition type liquid crystal device, or a White-Taylor type guest-host liquid crystal device. In this case, the compound may preferably be used in a proportion of 0.01–80 wt.% of the liquid crystal composition.

Further, the optically active compound represented by formula (II), when added in a proportion of, e.g., 0.01–80 wt.% to a liquid crystal composition which per se shows a chiral smectic liquid crystal state, can improve the characteristics such as durability. Further, when added to a smectic liquid crystal, it can provide a liquid crystal composition showing a ferroelectric chiral smectic phase. In this case, the compound may preferably be added in a proportion of 0.01–80 wt.% of the liquid crystal composition.

The mesomorphic compound represented by formula (I) may be controlled with respect to the type and the temperature range of its liquid crystal phase by adjusting the number of carbon atoms in the group $R_1$. The number of carbon atoms may generally be 1–18, while the number of 4–16, particularly 6–12, is preferred from the viscosity and the temperature range of SmC* phase.

The mesomorphic compounds represented by formula (I) may preferably be produced from the above mentioned 4-alkoxybenzenethiols of formula (II) as optically active intermediates.

The mesomorphic compounds may be produced from such optically active intermediates through processes, e.g., as shown in the following schemes (wherein $R_1$, $R*$ and $l$ are the same as defined above):

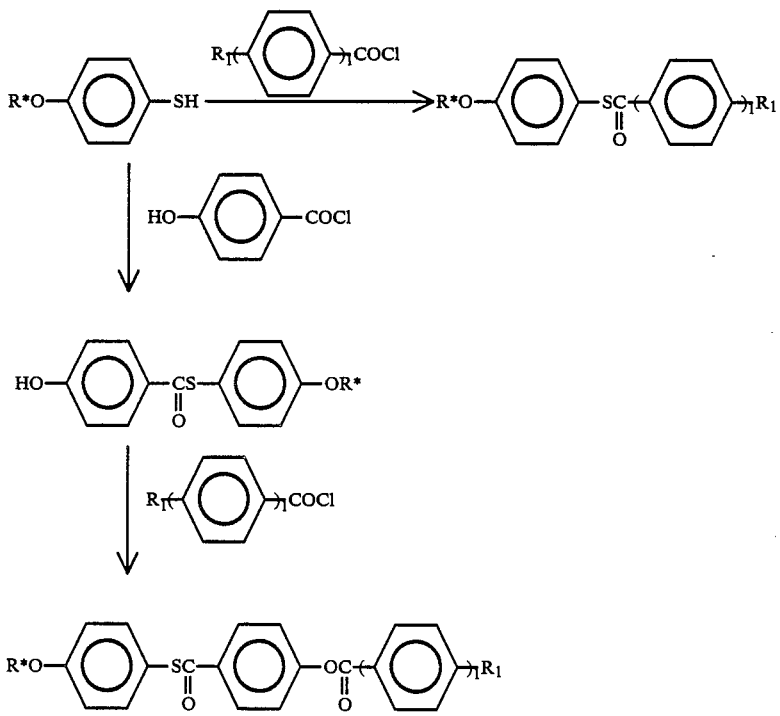

Specific examples of the mesomorphic compounds thus obtained include the following:
4-n-hexyloxythiobenzoic acid-S-4'-(2-methylbutyloxy)phenyl,
4-n-heptyloxythiobenzoic acid-S-4'-(2-methylbutyloxy)phenyl,
4-n-octyloxythiobenzoic acid-S-4'-(2-methylbutyloxy)phenyl,
4-n-nonyloxythiobenzoic acid-S-4'-(2-methylbutyloxy)phenyl,
4-n-decyloxythiobenzoic acid-S-4'-(2-methylbutyloxy)phenyl,
4-n-dodecyloxythiobenzoic acid-S-4'-(2-methylbutyloxy)phenyl,
4-n-hexadecyloxythiobenzoic acid-S-4'-(2-methylbutyloxy)phenyl,
4-n-hexylthiobenzoic acid-S-4'-(2-methylbutyloxy)phenyl,
4-n-decylthiobenzoic acid-S-4'-(2-methylbutyloxy)phenyl,
4-n-tridecylthiobenzoic acid-S-4'-(2-methylbutyloxy)phenyl,
4'-n-hexyloxybiphenylthiocarboxylic acid-S-4'-(2-methylbutyloxy)phenyl,
4'-n-octyloxybiphenylthiocarboxylic acid-S-4'-(2-methylbutyloxy)phenyl,
4'-n-decyloxybiphenylthiocarboxylic acid-S-4'-(2-methylbutyloxy)phenyl,
4'-n-heptylbiphenylthiocarboxylic acid-S-4'-(2-methylbutyloxy)phenyl,
4-n-hexyloxybenzoic acid-4'-thiocarboxylic acid phenyl-S-4''-(2-methylbutyloxy)phenyl,
4-n-decyloxybenzoic acid-4'-thiocarboxylic acid phenyl-S-4''-(2-methylbutyloxy)phenyl,
4-n-dodecyloxybenzoic acid-4'-thiocarboxylic acid phenyl-S-4''-(2-methylbutyloxy)phenyl,
4-n-decylbenzoic acid-4'-thiocarboxylic acid phenyl-S-4''-(2-methylbutyloxy)phenyl,
4-n-pentyloxythiobenzoic acid-S-4'L -(3-methylpentyloxy)phenyl,
4-n-octyloxythiobenzoic acid-S-4'-(3-methylpentyloxy)phenyl,
4-n-decyloxythiobenzoic acid-S-4'-(3-methylpentyloxy)phenyl,
4-n-hexylthiobenzoic acid-S-4'-(3-methylpentyloxy)phenyl,
4'-n-octyloxybiphenylthiocarboxylic acid-S-4-(3-methylpentyloxy)phenyl,
4-n-hexyloxythiobenzoic acid-S-4'-(4-methylhexyloxy)phenyl,
4-n-decyloxythiobenzoic acid-S-4'-(4-methylhexyloxy)phenyl,
4-n-heptylthiobenzoic acid-S-4'-(4-methylhexyloxy)phenyl,
4-n-hexyloxythiobenzoic acid-S-4'-(1-methylpropoxy)phenyl,
4-n-decyloxythiobenzoic acid-S-4'-(1-methylpropoxy)phenyl,
4-n-octyloxythiobenzoic acid-S-4'-(1-methylhexyloxy)phenyl,
4-n-dodecyloxythiobenzoic acid-S-4'-(1-methylpentyloxy)phenyl,
4-n-hexylthiobenzoic acid-S-4'-(1-methylpentyloxy)phenyl,
4-n-octyloxythiobenzoic acid-S-4'-(1,3-dimethylpropoxy)phenyl,
4-n-tridecyloxythiobenzoic acid-S-4'-(1,3-dimethylpropoxy)phenyl, 4-n-heptyloxythiobenzoic acid-S-4'-(1-methylheptyloxy)phenyl,
4-n-octyloxythiobenzoic acid-S-4'-(1-methylheptyloxy)phenyl,
4-n-hexyloxythiobenzoic acid-S-4'-(1-methylbutoxy)phenyl,
4-n-octyloxythiobenzoic acid-S-4'-(2-methyloctyloxy)phenyl,
4-n-decyloxythiobenzoic acid-S-4'-(2-methylnonyloxy)phenyl,
4-n-heptyloxythiobenzoic acid-S-4'-(2-methyldecyloxy)phenyl,
4-n-pentylthiobenzoic acid-S-4'-(2-methyldecyloxy)phenyl,
4'-n-hexyloxybiphenylthiocarboxylic acid-S-4-(2-methyldecyloxy)phenyl.

In the following Table 1, some specific examples with R* being 2-methylbutyl are listed along with their phase transition temperatures. In the table, the numerals indicate temperature in Celsius. In Table 1 and other parts of this specification, the symbols respectively denote the following phases:

Cryst.: crystal phase
SmA: smectic A phase
SmC*: chiral smectic C phase
N: nematic phase
Ch: cholesteric phase
Iso.: isotropic phase
Sm1, Sm2, Sm3: smectic phase (unidentified) other than SmA and SmC*

TABLE 1

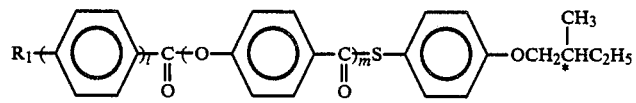

| Example | $R_1$ | l | m | Phase transition temperature |
|---|---|---|---|---|
| 5 | n-$C_8H_{17}O-$ | 1 | 0 | Cryst. $\underset{39}{\overset{65}{\rightleftarrows}}$ Ch. $\underset{74}{\overset{76}{\rightleftarrows}}$ Iso.; SmC* at 62 |
| 6 | n-$C_{10}H_{21}O-$ | 1 | 0 | Cryst. $\underset{33}{\overset{57}{\rightleftarrows}}$ SmC* $\underset{70}{\overset{72}{\rightleftarrows}}$ Ch. $\underset{75}{\overset{77}{\rightleftarrows}}$ Iso. |
| 7 | n-$C_8H_{17}O-$ | 2 | 0 | Cryst. $\underset{90}{\overset{95}{\rightleftarrows}}$ Sm2 $\underset{122}{\overset{126}{\rightleftarrows}}$ Sm1 $\underset{141}{\overset{144}{\rightleftarrows}}$ SmC* $\underset{194}{\overset{197}{\rightleftarrows}}$ SmA $\underset{204}{\overset{207}{\rightleftarrows}}$ Ch. $\underset{207}{\overset{210}{\rightleftarrows}}$ Iso. |
| 8 | n-$C_{10}H_{21}O-$ | 2 | 0 | Cryst. $\underset{}{\overset{83}{\rightleftarrows}}$ Sm2 $\underset{119}{\overset{122}{\rightleftarrows}}$ Sm1 $\underset{139}{\overset{142}{\rightleftarrows}}$ SmC* $\underset{197}{\overset{200}{\rightleftarrows}}$ SmA $\underset{202}{\overset{205}{\rightleftarrows}}$ Iso. |
| 9 | n-$C_7H_{15}-$ | 2 | 0 | Cryst. $\underset{}{\overset{43}{\rightleftarrows}}$ Sm2 $\underset{24}{\overset{62}{\rightleftarrows}}$ Sm1 $\underset{138}{\overset{142}{\rightleftarrows}}$ SmC* $\underset{153}{\overset{156}{\rightleftarrows}}$ SmA $\underset{180}{\overset{183}{\rightleftarrows}}$ Ch. $\underset{187}{\overset{190}{\rightleftarrows}}$ Iso. |
| 10 | n-$C_6H_{13}-$ | 1 | 0 | Cryst. $\underset{-9.6}{\overset{46.7}{\rightleftarrows}}$ Iso.; Ch. at 22.4 |
| 11 | n-$C_{12}H_{25}O-$ | 1 | 0 | Cryst. $\underset{41}{\overset{63}{\rightleftarrows}}$ SmC* $\underset{75}{\overset{77}{\rightleftarrows}}$ SmA $\underset{}{\overset{78}{\rightleftarrows}}$ Iso. |
| 12 | n-$C_{13}H_{27}-$ | 1 | 0 | Cryst. $\underset{-9.1}{\overset{18.4}{\rightleftarrows}}$ Sm2 $\underset{-3.1}{\overset{25.6}{\rightleftarrows}}$ Sm1 $\underset{34.8}{\overset{38.2}{\rightleftarrows}}$ SmA $\underset{44.1}{\overset{47.5}{\rightleftarrows}}$ Iso. |

TABLE 1-continued

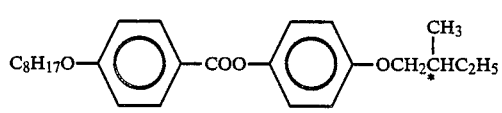

| Example | R₁ | l | m | Phase transition temperature |
|---|---|---|---|---|
| 13 | n-C₁₆H₃₃O— | 1 | 0 | Cryst. $\xrightarrow{67.9}$ SmC* $\underset{73.7}{\overset{76.1}{\rightleftarrows}}$ SmA $\underset{76.1}{\overset{79.5}{\rightleftarrows}}$ Iso. ; 45.1, 51.3, Sm1 |
| 14 | n-C₁₂H₂₅O— | 1 | 1 | Cryst. $\underset{79.6}{\overset{92.3}{\rightleftarrows}}$ SmC* $\underset{158.6}{\overset{162.6}{\rightleftarrows}}$ Ch. $\underset{177.4}{\overset{181.8}{\rightleftarrows}}$ Iso. |
| 15 | n-C₁₀H₂₁— | 1 | 1 | Cryst. $\xrightarrow{99.4}$ SmC* $\underset{125.1}{\overset{127.5}{\rightleftarrows}}$ Ch. $\underset{161.4}{\overset{164.1}{\rightleftarrows}}$ Iso. ; 64.9, 86.4, Sm2 $\underset{82.8}{\leftarrow}$ Sm1 |

The liquid crystal composition according to the present invention contains at least one species of the mesomorphic compound represented by formula (I). For example, the mesomorphic compound represented by formula (I) may be mixed with a ferroelectric liquid crystal selected from those of the formulas (a)–(m) shown below to lower and enlarge the temperature range of SmC*. In this case, it is preferred to use the mesomorphic compound represent by formula (I) in an amount constituting 1–99 wt.%, particularly 5–95 wt.% of the resulting liquid crystal composition.

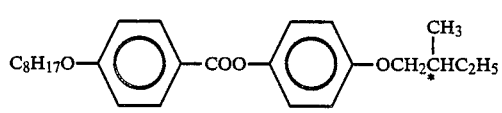

(a)

4-octyloxybenzoic acid-4'-(2-methyloxy)phenyl ester

Cryst. $\xrightarrow{42}$ SmC* $\xrightarrow{43.5}$ SmA $\xrightarrow{58.5}$ Ch. $\xrightarrow{62}$ Iso.

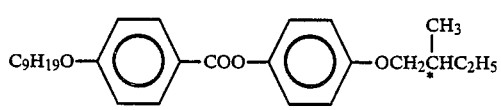

(b)

4-nonyloxybenzoic acid-4'-(2-methylbutyloxy)-phenyl ester

Cryst. $\xrightarrow{44}$ SmA $\xrightarrow{60}$ Iso. ; 43.5 SmC*

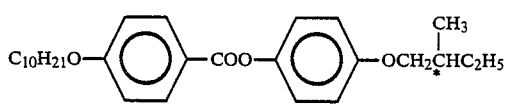

(c)

4-decyloxybenzoic acid-4'-(2-methylbutyloxy)-phenyl ester

Cryst. $\xrightarrow{44}$ SmC* $\xrightarrow{50}$ SmA $\xrightarrow{65}$ Iso.

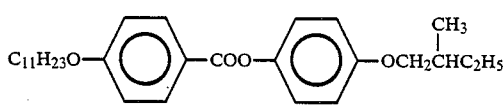

(d)

4-undecyloxybenzoic acid-4'-(methylbutyloxy)-phenyl ester

Cryst. —49.5→ SmA —63→ Iso.
              ↓ 48
              SmC*

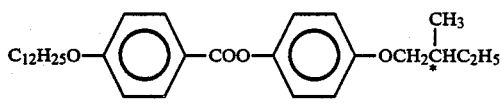 (e)

4-dodecyloxybenzoic acid 4'-(2-methylbutyloxy)-phenyl ester

Cryst. —49→ SmC* —52→ SmA —65→ Iso.

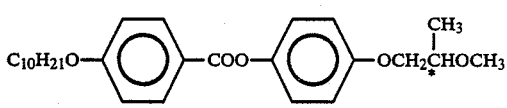 (f)

4-decyloxybenzoic acid 4'-(2-methylbutyloxy)-phenyl ester

Cryst. —40→ SmA —47→ Iso.
   ↖17      ↓28
   Sm1 ←23— SmC*

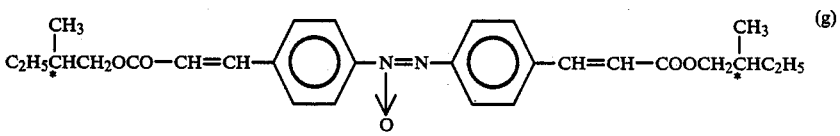 (g)

4,4'-azoxycinnamic acid bis(2-methylbutyl) ester

Cryst. ⇌121⇌ SmC* ⇌134⇌ SmA ⇌168⇌ Iso.

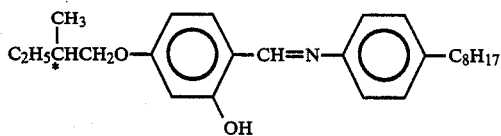 (h)

4-o-(2-methyl)butylresorcylidene-4'-octylaniline (MBRA 8)

Cryst. ⇌28⇌ SmC* ⇌55⇌ SmA ⇌62⇌ Iso.

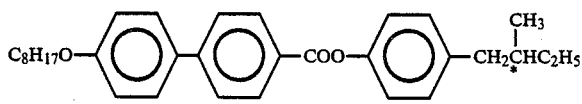 (i)

4-(2'-methylbutyl)phenyl-4'-octyloxybiphenyl-4-carboxylate

Cryst. ⇌78⇌ Sm3 ⇌80⇌ SmC* ⇌128.3⇌ SmA ⇌171.0⇌ Ch. ⇌174.2⇌ Iso.

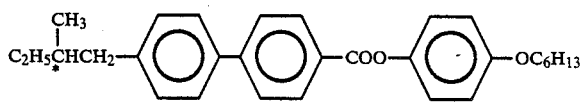 (j)

4-hexyloxyphenyl-4-(2''-methylbutyl)biphenyl-4'-carboxylate

Cryst. ⇌68.8⇌ SmC* ⇌80.2⇌ Ch. ⇌163.5⇌ Iso.

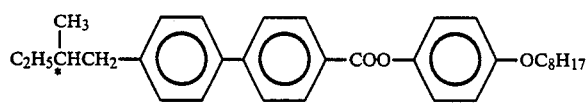

4-octyloxyphenyl-4-(2''-methylbutyl)biphenyl-4'-carboxylate

Cryst. ⇌ 76 SmC* ⇌ 88.6 Ch. ⇌ 155.4 Iso.

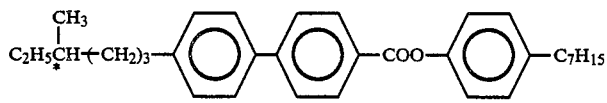

4-heptylphenyl-4-(4''-methylhexyl)biphenyl-4'-carboxylate

Cryst. ⇌ 91.5 SmC* ⇌ 93 SmA ⇌ 112 Ch. ⇌ 131 Iso.

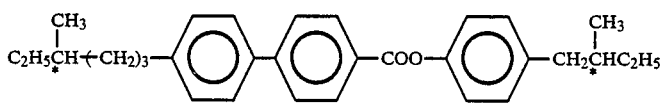

4-(2''-methylbutyl)phenyl-4-(4''-methylhexyl)-biphenyl-4'-carboxylate

Cryst. →83.4 Ch. →114 Iso.
↓81.0
SmC* →74.3 SmA

The mesomorphic compound represented by formula (I) may also be mixed with a smectic liquid crystal such as those of formulae (n)–(r) below which per se are not chiral to provide a composition which may be used as a ferroelectric liquid crystal. In this case, the mesomorphic compound represented by formula (I) may preferably be used in an amount of 1–99 wt.%, particularly 5–95 wt.%.

(n)

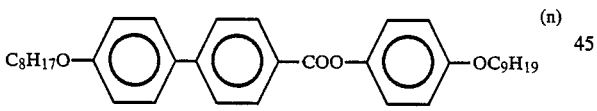

(4-nonyloxyphenyl)-4'-octyloxybiphenyl-4-carboxylate

Cryst. ⇌ 107 / 74 SmB ⇌ 117 SmC ⇌ 160 SmA ⇌ 195 Iso.

(o)

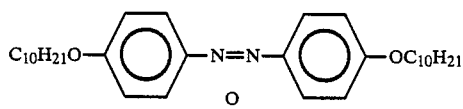

4,4'-decyloxyazoxybenzene

Cryst. → 77 SmC ⇌ 120 N ⇌ 123 Iso.

(p)

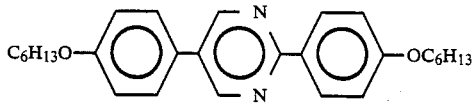

2-(4'-hexyloxyphenyl)-5-(4-hexyloxyphenyl)-pyrimidine

Cryst. → 120 SmC ⇌ 189 SmA ⇌ 216 Iso.

(q)

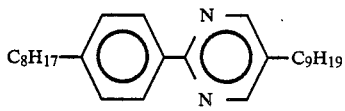

2-(4'-octyloxyphenyl-5-nonylpyrimidine

Cryst. → 33 SmC ⇌ 60 SmA ⇌ 75 Iso.

(r)

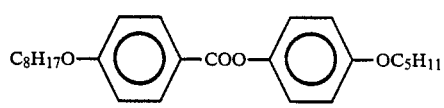

4'-pentyloxyphenyl-4-octylazoxybenzoate

Cryst. → 58 SmC → 64 SmA → 66 N → 85 Iso.

Herein, the symbols respectively denote the following phases:
Cryst.: crystal phase
SmA: smectic A phase
SmB: smectic B phase
SmC: smectic C phase
N: nematic phase
Iso.: isotropic phase.

As described above, the 4-(alkoxy)benzenethiol and bis(4-alkoxyphenyl)disulfide according to the present invention can be combined with an intermediate for a functional material having appropriate intermolecular force and shape without imparing an optical activity, and susceptible of arbitrary molecular designing. Particularly, by changing the length of the alkyl chain, it is possible to control the kind and the temperature range of the liquid crystal state to be developed.

Further, the 4-(alkoxy)benzenethiol and bis(2-alkoxyphenyl)disulfide according to the present invention may be mixed to provide a chiral nematic liquid crystal composition or a chiral smectic liquid crystal composition having improved performances.

The mesomorphic compound represented by formula (I) according to the present invention, which may be readily derived from the above mentioned 4-(alkoxy)benzenethiol, shows SmC* phase at a relatively low temperature and also stably shows SmC* phase in a wide temperature range, so that it is effectively used as a material for a ferroelectric liquid crystal. Further, the liquid crystal composition containing at least one species of the mesomorphic compound represented by formula (I) has improved performances through lowering and enlargement in the temperature range for SmC* phase.

The present invention will be explained more specifically with reference to some examples.

EXAMPLE 1

Bis(4-(2'-methylbutoxy)phenyl)disulfide

1st step

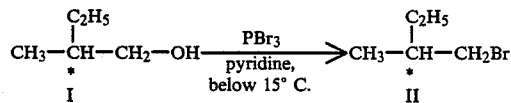

700.0 g (7.941 mol) of I was dissolved in 281 g of pyridine, cooled with ice, and 853 g (3.15 mol) of $PBr_3$ was gradually added dropwise. After 6 hours, the mixture was subjected to reduced-pressure distillation (70°–74° C., 150–50 mmHg, 3.4 hr.) to obtain 699 g of crude II, which was then extracted with 2.3 liter of petroleum ether, washed with 1650 ml of 5% NaOH for 3 times, with 1650 ml of $H_2O$ for 3 times, with 1650 ml of 10% $H_2SO_4$ for 2 times, with 1200 ml of conc. $H_2SO_4$ for 2 times and with 1500 ml of $H_2O$ for 3 times, followed by drying with $Na_2SO_4$, subjected to distilling-off the solvent, rectified to obtain 549.8 g (3.640 mol). Yield 45.8%.

2nd step

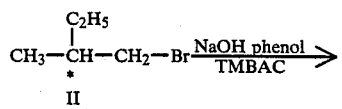

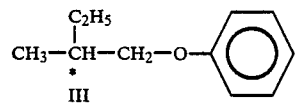

381.0 g (2.522 mol) of II, 265 g of phenol, 1000 ml of $H_2O$ and 15 g of trimethylbenzylammonium chloride were charged in a round-bottomed flask, and boiled, and 96 g of NaOH dissolved in 320 ml of $H_2O$ was added dropwise. The mixture was subjected to reaction at 90°–102° C. for 40 hours, followed by extraction with 2.0 liter of IPE, washed with 800 ml of 5% NaOH for 2 times, drying and distilling-off the solvent to obtain 296.4 g (1.805 mol) of III. Purity 95%, Yield 71.6%.

3rd step

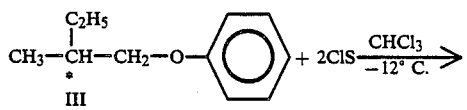

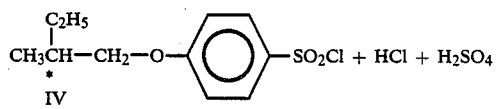

307.4 g (1.872 mol) of III was dissolved in 770 ml of $CHCl_3$, and 436.8 g of $ClSO_3H$ was added dropwise on an ice bath ($-12°$ C.). After 2.5 hrs, the completion of the reaction was confirmed by TLC, and the mixture was poured on ice, followed by extraction with 3.0 l of $CHCl_3$, washing with water, drying, and distilling-off the solvent to obtain 247.0 g of a crude product. The product was purified with column chromatography (silica gel: 2.5 kg, element=n-hexane:IPE=5:1) to obtain 200.6 g (0.763 mol) of IV. Yield 40.8%.

The following IR (infrared absorption) and NMR (nuclear magnetic resonance) data were obtained:

IR: 2990 $cm^{-1}$, 1950 $cm^{-1}$, 2900 $cm^{-1}$, 1600 $cm^{-1}$, 1385 $cm^{-1}$, 1280 $cm^{-1}$, 1175 $cm^{-1}$

NMR: 8.1–6.9 ppm (q, 4H), 3.9 ppm (d, 2H), 2.1–0.8 ppm (m, 9H)

4th step

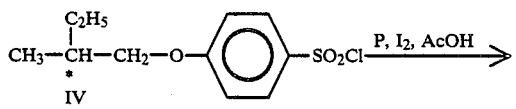

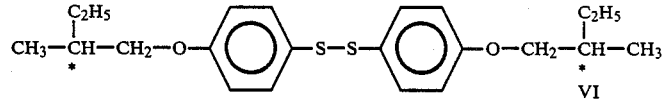

A mixture of 45.9 g of red phosphorus, 1.863 g of $I_2$ and 36.8 ml of AcOH was heated, and on boiling, 16 g (1/10) of IV was added dropwise. When $I_2$ gas was evolved, 144.6 g (9/10) of IV was added dropwise, and the mixture was refluxed. When the reaction was no more proceeded, 1.86 g of $I_2$ was added. When, $I_2$ gas completely disappeared, 36.7 ml of $H_2O$ was added, followed by 1 hour of further heating, 8 hours of standing at 85° C., extraction with 1.2 liter of IPE, washing with water, drying and distilling-off the solvent to obtain 150 g of a crude product. The product was separated by silica gel-column chromatography. The product showed the following data:

Optical rotation: $[\alpha]_D^{29°\ C} = +7.6°$

IR: 2970 cm$^{-1}$, 2930 cm$^{-1}$, 2880 cm$^{-1}$, 1600 cm$^{-1}$, 1500 cm$^{-1}$, 1465 cm$^{-1}$, 1282 cm$^{-1}$, 1250 cm$^{-1}$

NMR: 7.5–6.8 ppm (q, 4H), 3.8 ppm (d, 2H), 2.1–0.8 ppm (m, 9H)

EXAMPLE 2

4-(2'-methylbutoxy)benzenethiol

1st step

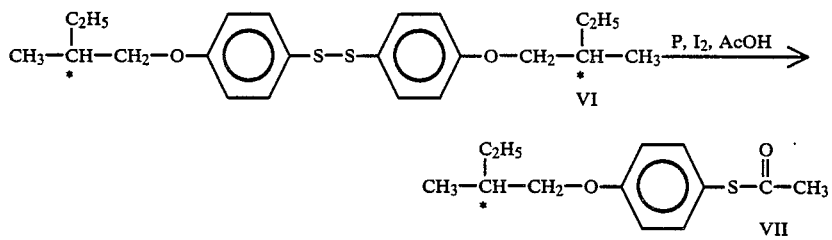

10 g of VI prepared in the same manner as in Example 1 was reduced again in the same manner as in the fourth step of Example 1, poured in the same amount of water, followed by extraction with IPE, drying, filtration and distilling off the solvent to obtain 8.7 g of VII.

IR: 2980 cm$^{-1}$, 2950 cm$^{-1}$, 2900 cm$^{-1}$, 1720 cm$^{-1}$, 1620 cm$^{-1}$, 1520 cm$^{-1}$, 1260 cm$^{-1}$, 1130 cm$^{-1}$

NMR: 7.3–6.8 ppm (q, 4H), 3.8 ppm (d, 2H) 2.3 ppm (S, 3H), 2.1–0.8 ppm (m, 9H)

2nd step

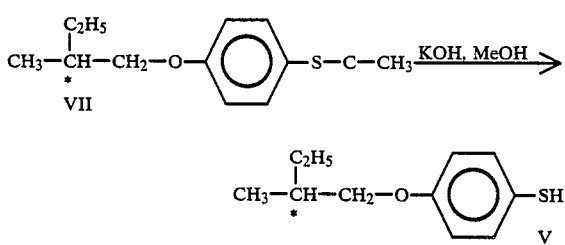

The reaction product was neutralized, extracted with 150 ml of IPE, washed with water and subjected to distillation of the solvent to obtain 6.9 g of a crude product. By reduced-pressure distillation (2 mmHg, 68°–94° C.), the —SH product was isolated in an amount of 2.2291 g.

Optical rotation: $[\alpha]_D^{29°\ C} = 6.1°$

IR: 2980 cm$^{-1}$, 2940 cm$^{-1}$, 2890 cm$^{-1}$, 2580 cm$^{-1}$, 1610 cm$^{-1}$, 1505 cm$^{-1}$, 1255 cm$^{-1}$, 1295 cm$^{-1}$

NMR: 7.3–6.7 ppm (q, 4H), 3.8–3.7 ppm (q, 2H), 3.3 ppm (S, 1H), 1.8–0.8 ppm (m, 9H)

EXAMPLE 3

A twisted nematic (TN) cell prepared by use of a liquid crystal mixture comprising 1 wt. part of (+)-4-(2'-methyl)butoxybenzenethiol of Example 2 of the present invention added to 99 wt. parts Rikson GR-63 (biphenyl liquid crystal mixture produced by Chisso K.K.) was observed to provide a nematic phase with greatly reduced reverse domain as compared with a TN cell prepared without addition of the thiol.

EXAMPLE 4

A twisted nematic (TN) cell prepared by use of a liquid crystal mixture comprising 1 wt. part of (+)-bis(4-(2'-methylbutoxy)phenyl)disulfide of Example 1 of the present invention added to 99 wt. parts Rikson GR-63 (biphenyl liquid crystal mixture produced by Chisso K.K.) was observed to provide a nematic phase with greatly reduced reverse domain as compared with a TN cell prepared without addition of the thiol.

EXAMPLE 5

4-octyloxythiobenzoic acid-S-4'-(2-methylbutyloxy)phenyl 20 ml of SOCl$_2$ was added to 4.0 g (1.6×10$^{-2}$ mol) of 4-octyloxybenzoic acid, and the mixture was refluxed under heating for 4 hours. Excessive SOCl$_2$ was distilled off to obtain 4-octyloxybenzoic acid chloride. 3.136 g (1.6×10$^{-2}$ mol) of 4-(2'-methylbutyloxy)benzenethiol and 1.246 g of pyridine were dissolved in 12 ml of toluene, cooled with ice, and the 4-octyloxybenzoic acid chloride dissolved in 10 ml of toluene was added thereto. The mixture was left standing at 5° C. for 45 min, followed by stirring for 3.5 hours at room temperature.

The reaction mixture was poured into cold water and acidified with 6N-HCl to precipitate a crystal, which was then separated by filtration. The organic layer was washed with water, 2N-NaOH solution and water, followed by drying with anhydrous Na$_2$SO$_4$ and distilling-off the solvent to obtain 7.9 g of an oily product.

The product was purified by silica gel-column chromatography and recrystallized from ethanol to obtain 2.3144 g of 4-octyloxythiobenzoic acid-S-4'-(2-methylbutyloxy)phenyl. Yield 33.8%.

The product provided the following IR and NMR data:

IR (cm$^{-1}$): 2930, 2870, 1675, 1605, 1500, 1475, 1265, 1250, 1170, 905, 840.

NMR (σppm): 8.1–6.8 (8H), 4.2–3.7 (4H), 2.0–0.9 (24H).

EXAMPLES 6, 10–13

Mesomorphic compounds according to the present invention were obtained in a similar manner as in Example 5. The products are enumerated in Table 1 appearing hereinbelow together with their phase transition temperatures.

EXAMPLE 7

4'-octyloxybiphenylthiocarboxylic acid-S-4-(2'-methylbutyloxy)phenyl 20 ml of SOCl$_2$ was added to 4.0 g (1.23×10$^{-2}$ mol) of 4-octyloxybiphenylcarboxylic acid, and the mixture was refluxed under heating for 5 hours to obtain 4-octyloxybiphenylcarboxylic acid chloride.

2.41 g (1.23×10⁻² mol) of 4-(2'-methylbutyloxy)benzenethiol and 972 mg of pyridine were dissolved in 12 ml of toluene, cooled with ice, and the 4-octyloxybiphenylcarboxylic acid chloride dissolved in 12 ml of toluene was added thereto. The mixture was thereafter stirred for 6 hours at room temperature.

The reaction mixture was poured into cold water and acidified with 6N-HCl to precipitate a crystal, which was then separated by filtration. The organic layer was washed with water, 2-N-NaOH solution and water, followed by drying with anhydrous $Na_2SO_4$ and distilling-off the solvent to obtain 8.5 g of an oily product.

The product was purified by silica gel-column chromatography to obtain 1.6 g of crystal. The crystal was further purified by column chromatography with n-hexane: MeOH=50:1 and recrystallized from ethanol to obtain 898 g of 4'-octyloxybiphenylthiocarboxylic acid-S-4-(2'-methylbutyloxy)phenyl.

The product showed the following IR and NMR data:

IR (cm⁻¹): 2925, 2850, 1670, 1600, 1500, 1250, 1190, 910, 830.

NMR (σppm): 8.1–6.8 (12H), 4.1–3.7 (4H), 2.1–0.9 (24H).

EXAMPLES 8 AND 9

Mesomorphic compounds according to the present invention were obtained in a similar manner as in Example 7. The products are enumerated in Table 1 appearing hereinbelow together with their phase transition temperatures.

EXAMPLE 14 p-dodecyloxybenzoic acid-p'-thiocarboxylic acid phenyl-S-p''-(2-methylbutyloxy)phenyl

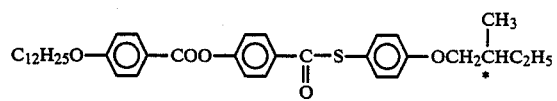

4.0 g (1.31×10⁻² mol) of p-dodecyloxybenzoic acid was dissolved in 15 ml of benzene, and 2.79 g (1.31×10⁻² mol) of $PCl_5$ was slowly added thereto under stirring at room temperature. Thereafter, 3 hours of heat-refluxing was effected, followed by distilling-off the solvent to obtain 4.4 g of p-dodecyloxybenzoic acid chloride.

P-acetyloxybenzoic acid (5.56×10⁻² mol) was dissolved in 45 ml of benzene, and 11.8 g (5.56×10⁻² mol) of $PCl_5$ was added in 6 fractions at an interval of 5 minutes each at room temperature. Then, the mixture was stirred for 20 minutes at room temperature, followed by heat-refluxing under stirring for 5 hours.

After distilling off the solvent, 12.7 g of p-acetyloxybenzoic acid chloride was obtained as a pale yellow oily product.

10.7 g (5.04×10⁻² mol) of 4-amyloxybenzenethiol and 3.98 g (5.04×10⁻² mol) of pyridine were dissolved in 30 ml of toluene, and a solution of 12.7 g of p-acetyloxybenzoic acid chloride in 30 ml of toluene was added dropwise thereto at 5° C. in 50 minutes. Thereafter, the mixture was stirred for 8 hours at room temperature.

After the completion of the reaction, the reaction mixture was poured in cold water and acidified with 6N-HCl. The resultant precipitate was filtered out, and the organic layer was washed with water, 2N-NaOH solution and water in this order, dried with anhydrous $Na_2SO_4$, followed by distillation of the solvent to obtain 19.0 g of a pale yellow oily product (p'-acetyloxythiocarboxylic acid phenyl-S-p''-(2-methylbutyloxyphenyl).

The thus obtained p'-acetyloxythiocarboxylic acid phenyl-S-p''-(2-methylbutyloxy)phenyl)was dissolved in 50 ml of methanol, and a mixture of methanol/N-H₄OH (28%)=1:1 was added thereto under stirring.

The mixture was poured in 150 ml of water, extracted with 100 ml of ether for 3 times, and the resultant ether layer was then washed with 100 ml of water for 3 times, followed by drying with anhydrous $Na_2SO_4$ and distilling-off the solvent to obtain 15.3 g of p-hydroxythiocarboxylic acid phenyl-S-p''-(2-methylbutyloxy)phenyl.

3.71 g (1.31×10⁻² mol) of the above obtained p-hydroxythiocarboxylic acid phenyl-S-p''-(2-methylbutyloxy)phenyl and 1.034 g (1.31×10⁻² mol) of pyridine were dissolved in 17 ml of toluene, and a solution of 4.4 g of decyloxybenzoic acid chloride in 12 ml of toluene was added dropwise thereto at 9° C. in 20 minutes. The mixture ws then stirred for 20 hours at room temperature.

After the reaction, the reaction mixture was poured in cold water ancd acidified with 6N-HCl solution. The resultant precipitate was filtered out, and the organic layer was washed with water, 2N-NaOH solution and water, followed by drying with anhydrous $Na_2SO_4$ and distilling-off the solvent to obtain 3.5 g of a crude product.

The product was purified by column chromatography to obtain 3.1 g of crystal, which was then recrystallized first from ethanol and then from ethyl acetate to obtain 1.1 g of p-dodecyloxybenzoic acid-p'-thiocarboxylic acid phenyl-S-p''-(2-methyloxy)phenyl.

The product showed the following data:

IR (cm⁻¹): 3930, 3855, 1740, 1685, 1620, 1600, 1500, 1475, 1265, 1210, 1170, 1070, 910.

NMR (σppm): 8.2–6.7 (12H), 4.2–3.7 (4H), 2.1–0.9 (32H).

EXAMPLE 15

P-decylbenzoic acid-p'-thiocarboxylic acid phenyl-S-p''-(2-methylbutyloxy)phenyl was synthesized in a similar manner as in Example 14. The product showed the following data:

IR (cm⁻¹): 2930, 2860, 1745, 1665, 1600, 1500, 1275, 1250, 1220, 1165, 1075, 910.

NMR (σppm): 8.3–6.9 (12H), 3.6–4.1 (d, 2H), 2.6–3.0 (t, 2H), 2.0–0.9 (28H).

EXAMPLE 16

A liquid crystal composition was prepared by mixing a known ferroelectric liquid crystal compound 4-octyloxybenzoic acid-4'-(2-methylbutyloxy)phenyl ester (shown below as "A") and 4-decyloxythiobenzoic acid-S-4'-(2-methylbutyloxy)phenyl ester (shown below as "B") prepared in Example 6. The change in phase transition temperature corresponding to compositional change of the resultant composition is shown as a phase diagram in the attached drawing.

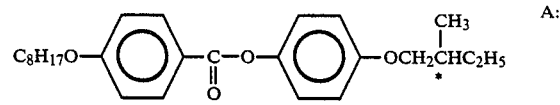

-continued

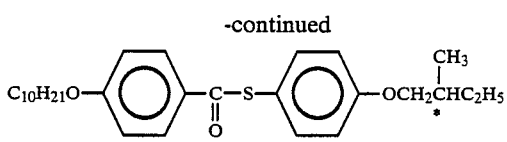

EXAMPLE 17

Liquid crystal device using the liquid crystal composition prepared in Example 16.

A 1000 Å-thick ITO film was applied as electrodes onto a highly polished glass substrate of 10×20 mm in sized, and an about 1000 Å-thick $SiO_2$ layer was deposited thereon by the ion beam process. On one of the thus tread pain of glass substrates, the liquid crystal composition of Example 16 was dropped, and the other substrate was superposed thereon. The substrates were held at 63° C. and mutually slided in a parallel movement while maintaining a spacing therebetween at 1.2 μm and observing through a polarizing microscope, whereby a homogenously aligned monodomain having lost spiral structure was observed to be formed. In this state, pulses of ±20 volts were applied at 50° C., whereby switching was effected at about 1 msec.

In this instance, a uniaxial alignment or orientation control treatment such as rubbing may also be applied instead of the parallel movement.

What is claimed is:

1. A mesomorphic compound represented by the following formula:

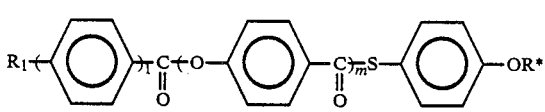

wherein $R_1$ is an alkyl group having 6–12 carbon atoms, R* is an alkyl group having 4–12 carbon atoms including an asymmetric carbon atom, l is 1 or 2, and m is 0 or 1.

2. A mesomorphic compound according to claim 1, wherein R* is 3-methylpentyl, 4-methylhexyl, 1-methylheptyl, 2-methylbutyl, 3-methyloctyl, 2-methylnonyl, or 2-methyldecyl.

3. A mesomorphic compound according to claim 1, which causes successive phase transition of isotropic phase, cholesteric phase and chiral smectic C phase in the course of temperature decrease.

4. A mesomorphic compound according to claim 1, which causes successive phase transition of isotrophic phase, cholesteric phase, smectic A phase, and chiral smectic C phase in the course of temperature decrease.

5. A mesomorphic compound according to claim 1, which is represented by the formula:

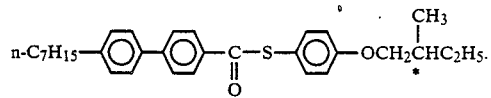

6. A mesomorphic compound according to claim 1, which is represented by the formula:

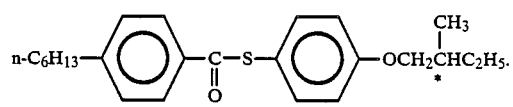

7. A mesomorphic compound according to claim 1, which is represented by the formula:

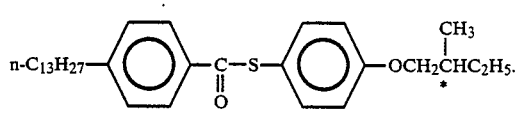

8. A mesomorphic compound according to claim 1, which is represented by the formula:

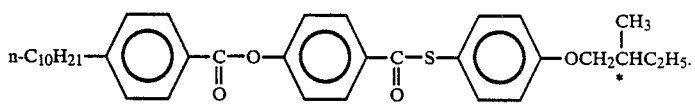

9. A mesomorphic compound represented by the following formula:

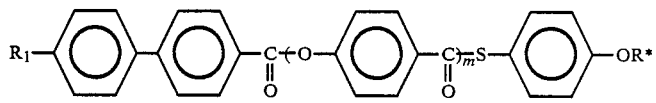

wherein $R_1$ is an alkyl or alkoxy group having 6–12 carbon atoms, R* is an alkyl group having 4–12 carbon atoms including an asymmetric carbon atom, and m is 0 or 1.

10. A mesomorphic compound according to claim 9, wherein R* is 3-methylpentyl, 4-methylhexyl, 1-methylheptyl, 2-methylbutyl, 3-methyloctyl, 2-methylnonyl, or 2-methyldecyl.

11. A mesomorphic compound according to claim 9, which causes successive phase transition of isotropic phase, cholesteric phase, smectic A phase, and chiral smectic C phase in the course of temperature decrease.

12. A mesomorphic compound according to claim 9, which is represented by the formula:

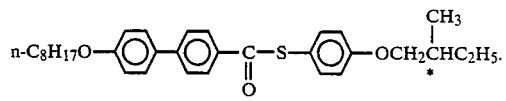

13. A mesomorphic compound according to claim 9, which is represented by the formula:

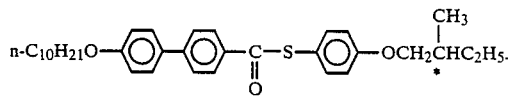

14. A mesomorphic compound represented by the following formula:

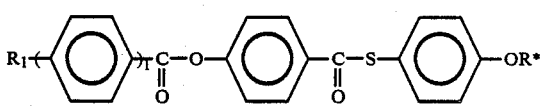

wherein $R_1$ is an alkyl or alkoxy grup having 6–12 carbon atoms, $R^*$ is an alkyl group having 4–12 carbon atoms including an asymmetric carbon atom, and l is 1 or 2.

15. A mesomorphic compound according to claim 14, wherein $R^*$ is 3-methylpentyl, 4-methylhexyl, 1-methylheptyl, 2-methylbutyl, 3-methyloctyl, 2-methylnonyl, or 2-methyldecyl.

16. A mesomorphic compound according to claim 14, which causes successive phase transition of isotropic phase, cholesteric phase and chiral smectic C phase in the course of temperature decrease.

17. A mesomorphic compound according to claim 14, which is represented by the formula:

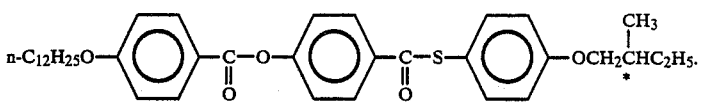

18. A chiral smectic liquid crystal composition comprising at least two compounds and containing at least one compound represented by the following formula:

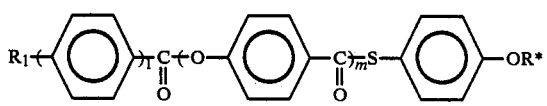

wherein $R_1$ is an alkyl group having 6–12 carbon atoms, $R^*$ is an alkyl group having 4–12 carbon atoms including an symmetric carbon atom, l is 1 or 2, and m is 0 or 1.

19. A liquid crystal composition according to claim 18, wherein $R^*$ is 3-methylpentyl, 4-methylhexyl, 1-methylheptyl, 2-methylbutyl, 3-methyloctyl, 2-methylnonyl, or 2-methyldecyl.

20. A chiral smectic liquid crystal composition comprising at least two components and containing at least one compound represented by the following formula:

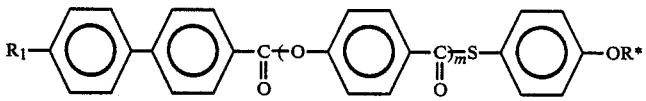

wherein $R_1$ is an alkyl or alkoxy group having 6–12 carbon atoms, $R^*$ is an alkyl group having 4–12 carbon atoms including an asymmetric carbon atom, and m is 0 or 1.

21. A liquid crystal composition according to claim 20, wherein $R^*$ is 3-methylpentyl, 4-methylhexyl, 1-methylheptyl, 2-methylbutyl, 3-methyloctyl, 2-methylnonyl, or 2-methyldecyl.

22. A chiral smectic liquid crystal composition comprising at least two components and containing at least one compound represented by the following formula:

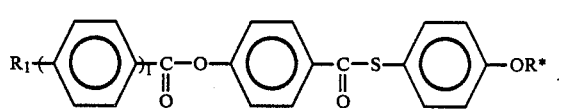

wherein $R_1$ is an alkylor alkoxy group having 6–12 carbon atoms, $R^*$ is an alkyl group having 4–12 carbon atoms including an asymmetric carbon atom, and l is 1 or 2.

23. A liquid crystal composition according to claim 22, wherein $R^*$ is 3-methylpentyl, 4-methylhexyl, 1-methylheptyl, 2-methylbutyl, 3-methyloctyl, 2-methylnonyl, or 2-methyldecyl.

24. A liquid crystal device, comprising:
a pair of substrates and a chiral smectic liquid crystal composition disposed between the substrates, said chiral smectic liquid crystal composition comprising at least two components and containing at least one compound represented by the following formula:

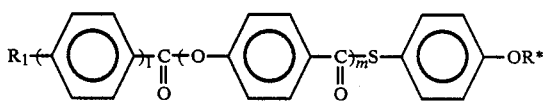

wherein $R_1$ is an alkyl or alkoxy grup having 6–12 carbon atoms, $R^*$ is an alkyl group having 4–12 carbon atoms including an asymmetric carbon atom, l is 1 or 2, and m is 0 or 1.

25. A liquid device according to claim 24, wherein said chiral smectic liquid crystal composition in chiral smectic C phase is formed in a layer having a thickness small enough to release the spiral structure.

26. A liquid crystal device according to claim 24, wherein at least one of said pair of substrates has beenn subjected to a uniaxial orientation treatment.

27. A liquid crystal device according to claim 24, wherein said uniaxial orientation treatment comprises rubbing.

28. A liquid crystal device, comprising:
a pair of substrates and a chiral smectic liquid crystal composition disposed between the substrates, said chiral smectic liquid crystal composition comprising at least two components and containing at least one compound represented by the following formula:

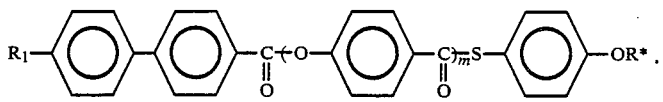

wherein $R_1$ is an alkyl or alkoxy group having 6–12 carbon atoms, $R^*$ is an alkyl grup having 4–12 carbon atoms including an asymmetric carbon atom, and m is 0 or 1.

29. A liquid crystal device according to claim 28, wherein $R^*$ is 3-methylpentyl, 4-methylhexyl, 1-methylheptyl, 2-methylbutyl, 3-methyloctyl, 2-methylnonyl, or 2-methyldecyl.

30. A liquid crystal device according to claim 28, wherein said chiral smectic liquid crystal composition in chiral smectic phase is formed in a layer having a thickness small enough to release the spiral structure.

31. A liquid crystal device according to claim 28, wherein at least one of said pair of substrates has been subjected to a uniaxial orientation treatment.

32. A liquid crystal device according to claim 28, wherein said uniaxial orientation treatment comprises rubbing.

33. A liquid crystal device, comprising:
a pair of substrates and a chiral smectic liquid crystal composition disposed between the substrates, said chiral smectic liquid crystal composition comprising at least two components and containing at least one compound represented by the following formula:

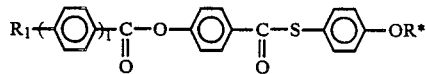

wherein $R_1$ is an alkyl or alkoxy group having 6–12 carbon atoms, $R^*$ is an alkyl group having 4–12 carbon atoms including an asymmetric carbon atom, and l is 1 or 2.

34. A liquid crystal device according to claim 33, wherein $R^*$ is 3-methylpentyl, 4-methylhexyl, 1-methylheptyl, 2-methylbutyl, 3-methyloctyl, 2-methylnonyl, or 2-methyldecyl.

35. A liquid crystal device according to claim 33, wherein said chiral smectic liquid crystal composition in chiral smectic C phase is formed in a layer having a thickness small enough to release the spiral structure.

36. A liquid crystal device according to claim 33, wherin at least one of said pair of substrates has been subjected to a uniaxial orientation treatment.

37. A liquid crystal device according to claim 33, wherein said uniaxial orientation treatment comprises rubbing.

38. A liquid crystal device according to claim 24, wherein $R^*$ is 3-methylpentyl, 4-methylhexyl, 1-methylheptyl, 2-methylbutyl, 3-methyloctyl, 2-methylnonyl or 2-methyldecyl.

* * * * *

UNITED STATES PATENT AND TRADEMARK OFFICE
CERTIFICATE OF CORRECTION

PATENT NO. : 4,876,027
DATED : October 24, 1989
INVENTOR(S) : KAZUO YOSHINAGA ET AL.     Page 1 of 3

It is certified that error appears in the above-identified patent and that said Letters Patent is hereby corrected as shown below: ON TITLE PAGE:

AT [56] REFERENCES CITED

Foreign Patent Documents, "59128357 7/1984 Japan" should read --59-128357 7/1984 Japan--.

AT [57] ABSTRACT

Line 3, "deviced" should read --derived--.

COLUMN 1

Line 8, "ARE" should read --AND--.
Line 22, "of" should be deleted.
Line 53, "a" should read --an--.

COLUMN 2

Line 16, "imparting" should read --imparing--.

COLUMN 3

Line 39, "they" should be deleted.

COLUMN 8

Line 39, "acid-S-4'L" should read --acid-S-4'--.

COLUMN 12

Line 26, "represent" should read --represented--.

UNITED STATES PATENT AND TRADEMARK OFFICE
CERTIFICATE OF CORRECTION

PATENT NO. : 4,876,027
DATED : October 24, 1989
INVENTOR(S) : KAZUO YOSHINAGA ET AL.          Page 2 of 3

It is certified that error appears in the above-identified patent and that said Letters Patent is hereby corrected as shown below:

COLUMN 18

Line 41, "1950 cm$^{-1}$," should read --2950 cm$^{-1}$,--.

COLUMN 20

Line 30, "3.136g" should read --¶ 3.136g--.

COLUMN 22

Line 7, "phenyl) was" should read --phenyl was--.
Line 22, "ws" should read --was--.
Line 25, "ancd" should read --and--.

COLUMN 23

Line 13, "sized," should read --size,--.
Line 15, "tread pain" should read --treated pair--.

COLUMN 25

Line 9, "grup" should read --group--.
Line 43, "symmetric carbon atom," should read --asymmetric carbon atom,--.

UNITED STATES PATENT AND TRADEMARK OFFICE
CERTIFICATE OF CORRECTION

PATENT NO. : 4,876,027
DATED : October 24, 1989
INVENTOR(S) : KAZUO YOSHINAGA ET AL.   Page 3 of 3

It is certified that error appears in the above-identified patent and that said Letters Patent is hereby corrected as shown below:

COLUMN 26

Line 10, "alkylor" should read --alkyl or--.
    Line 40, "grup" should read --group--.
    Line 44, "liquid device" should read
         --liquid crystal device--.
    Line 49, "beenn" should read --been--.

COLUMN 27

Line 12, "grup" should read --group--.

COLUMN 28

Line 26, "wherin" should read --wherein--.

Signed and Sealed this

Thirteenth Day of August, 1991

*Attest:*

HARRY F. MANBECK, JR.

*Attesting Officer*   *Commissioner of Patents and Trademarks*